US006178577B1

(12) United States Patent
Chien-Chuan

(10) Patent No.: US 6,178,577 B1
(45) Date of Patent: Jan. 30, 2001

(54) MATTRESS WITH ADJUSTABLE MASSAGE UNITS

(76) Inventor: Cheng Chien-Chuan, 9F-1, No. 396, Sec. 1, Nei-Hu Road, Taipei (TW)

( * ) Notice: Under 35 U.S.C. 154(b), the term of this patent shall be extended for 0 days.

(21) Appl. No.: 09/540,181

(22) Filed: Mar. 31, 2000

(51) Int. Cl.[7] .............................. A47C 31/00; A61M 1/00
(52) U.S. Cl. ...................................... 5/694; 5/915; 601/57
(58) Field of Search ................................ 5/694, 690, 915, 5/713, 658; 601/57, 55

(56) References Cited

U.S. PATENT DOCUMENTS 2,425,655 * 8/1947 Tompkins ................................. 5/915
4,326,506 * 4/1982 Kawabata ............................... 601/57
5,007,410 * 4/1991 DeLaney ................................. 5/694
5,437,607 * 8/1995 Taylor .................................... 601/57
5,437,608 * 8/1995 Cutler .................................... 601/57
5,606,754 * 3/1997 Hand et al. ............................. 5/713

* cited by examiner

*Primary Examiner*—Alexander Grosz
(74) *Attorney, Agent, or Firm*—W. Wayne Liauh

(57) ABSTRACT

A mattress having multiple massage units provided on a top surface thereof is provided. Each of the massage units is formed at a lower side with an open-ended space through which two long locating strips are extended. The long locating strips are sewed up onto the top surface of the mattress at points that are in front of and behind each massage unit by a predetermined distance, so that the massage units are attached to the mattress by the long locating strips while being movable between two sewed points of the long strips before and after them. The massage units are provided in their inner spaces with at least one pair of massage elements to massage different areas on a user's body.

7 Claims, 5 Drawing Sheets

MATTRESS WITH ADJUSTABLE MASSAGE UNITS

BACKGROUND OF THE INVENTION

The present invention relates to a mattress, and more particularly to a mattress with multiple massage units longitudinally movably attached to a top surface thereof, so that the same one mattress is adaptable to massage users of different heights.

With the quick development in the sciences of communication and information in the nowaday business society, people seem to spend more time sitting still during work and tend to get sore limbs and ached back more frequently. When lacking of adequate treatment or rehabilitation, the sore limbs and ached back would very possibly develop into worse conditions. To enable general consumers to conveniently treat their sore limbs and ached back at home, there are many types of massage devices developed and available in the market.

Among many common massage devices, there are large-sized massage lounges and massage mattresses and small-sized massage rods. Speaking of the massage mattress, it is a massage means requiring least strength to operate. A user needs only to lie on the mattress to have the whole body well massaged. Therefore, the massage mattress is most suitable for the aged and sick people and is most effective in reducing the probability of bedsore.

A conventional massage mattress usually includes several massage units that are concealed and fixedly mounted in the mattress and are therefore not movable in their position. It is therefore possible the massage mattress having fixed and concealed massage units does not match with the heights of different family members to meet everyone's need. Moreover, since the massage units are fixed to only a few predetermined points inside the mattress, they do not massage and accordingly treat all sore and ached areas on the user's body.

SUMMARY OF THE INVENTION

It is therefore a primary object of the present invention to provide a mattress with adjustable massage units, so that a user may freely adjust the position of the massage units on the mattress according to his height and actual need. That is, the mattress of the present invention is adaptable to users of different heights.

Another object of the present invention is to provide a mattress with multiple position-adjustable massage units that include a shoulder massage unit, a back massage unit, a waist massage unit, a thigh massage unit, and a shank massage unit to massage almost all areas on a user's body.

To achieve the above and other objects, the mattress of the present invention mainly includes multiple massage units that are provided on a top surface of the mattress at positions generally corresponding to a man's shoulders, back, waist, thighs and shanks. Each of the massage units is formed at a lower side with an open-ended space through which two long locating strips are extended. The long locating strips are sewed up onto the top surface of the mattress at points that are in front of and behind each massage unit by a predetermined distance, so that the massage units are attached to the mattress by the long locating strips while being movable between two sewed points of the long locating strips before and after them. The massage units are provided in their inner spaces with at least one pair of massage elements to massage different areas on a user's body by means of compression or vibration. To enhance the massage effect at waist, thighs and shanks, binding loops may be added to top surfaces of the massage units particularly for these areas, so that the user's waist, thighs and shanks are enclosed in the binding loops when the massage elements act to compress or vibrate these areas.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENTS

Figure 1:
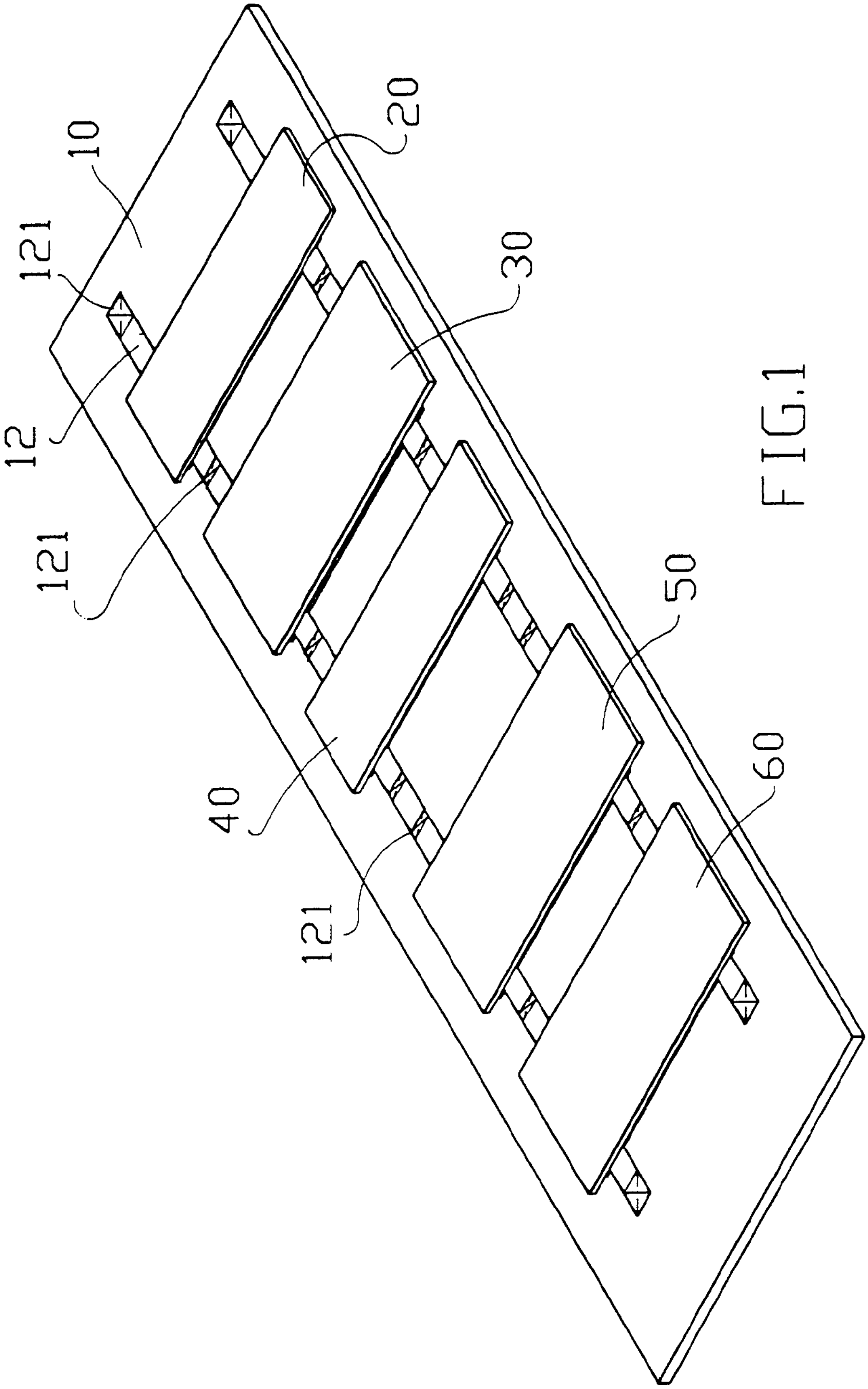
FIG. 1 is an assembled perspective of a mattress with adjustable massage units according to an embodiment of the present invention.
Figure 2:
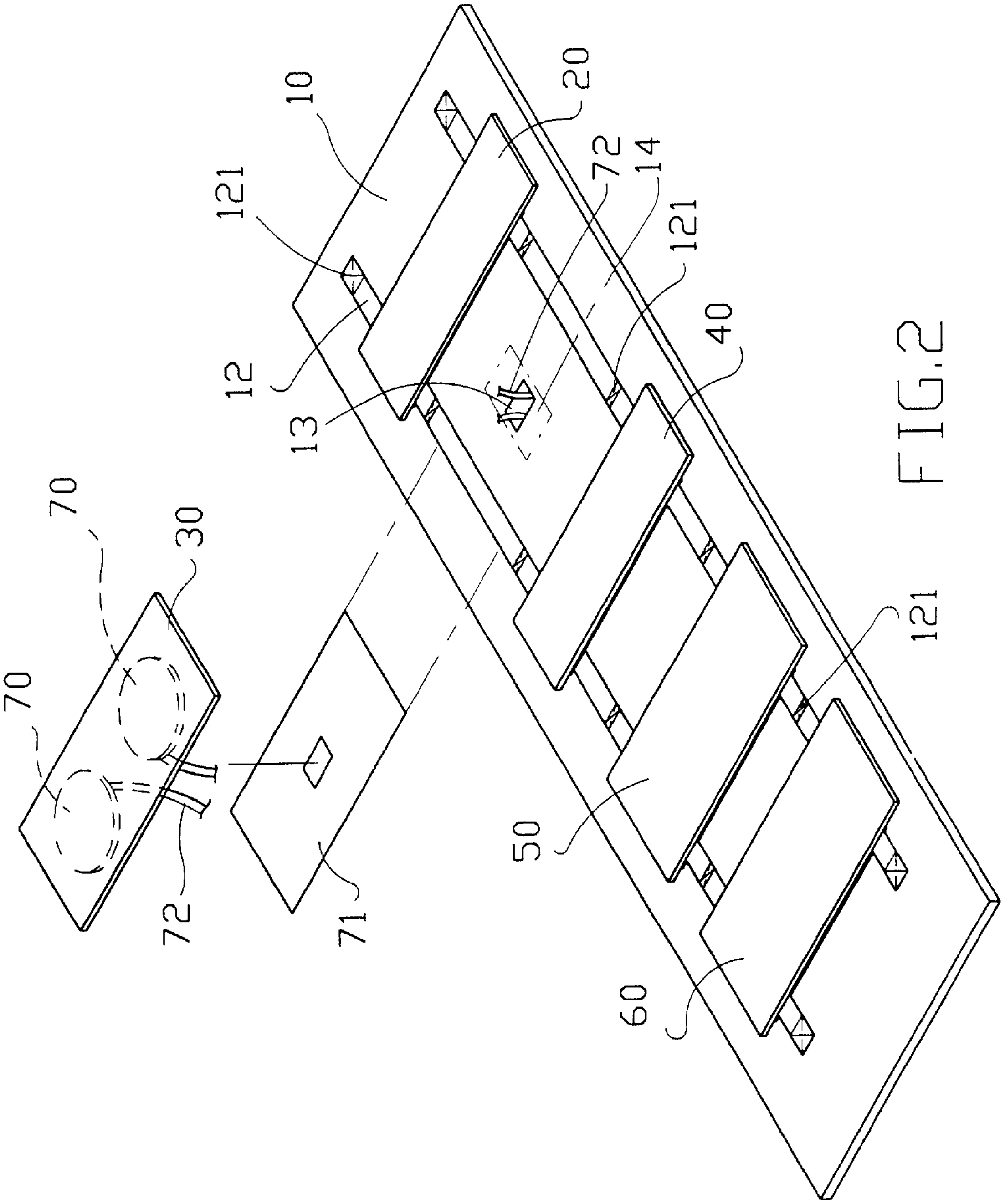
FIG. 2 is a partially exploded perspective of the mattress of FIG. 1.

Please refer to FIGS. 1 and 2 that are assembled and partially exploded perspective views, respectively, of a mattress according to an embodiment of the present invention. As shown, the mattress mainly includes a main body 10 and multiple massage units movably provided on a top surface of the mattress 10. These massage units usually sequentially include from top to bottom of the mattress 10, as illustrated in FIG. 1, a shoulder massage unit 20, a back massage unit 30, a waist massage unit 40, a thigh massage unit 50, and a shank massage unit 60. Each of these massage units 20 thru 60 is formed at a lower side facing the mattress 10 with an open-ended space 11 (see FIG. 4). Two long locating strips 12 are adapted to sequentially extend through all the open-ended spaces 11 to locate near two lateral edges of the spaces 11. Points on the long locating strips 12 at some distance in front of and behind each of the massage units 20 thru 60 are sewed up onto the mattress 10 to form sewed lines 121, so that each of the massage units 20 thru 60 is attached to the top surface of the mattress 10 but allowed to move in a longitudinal direction of the mattress 10 between two sewed lines 121 before and after it.

Figure 3:
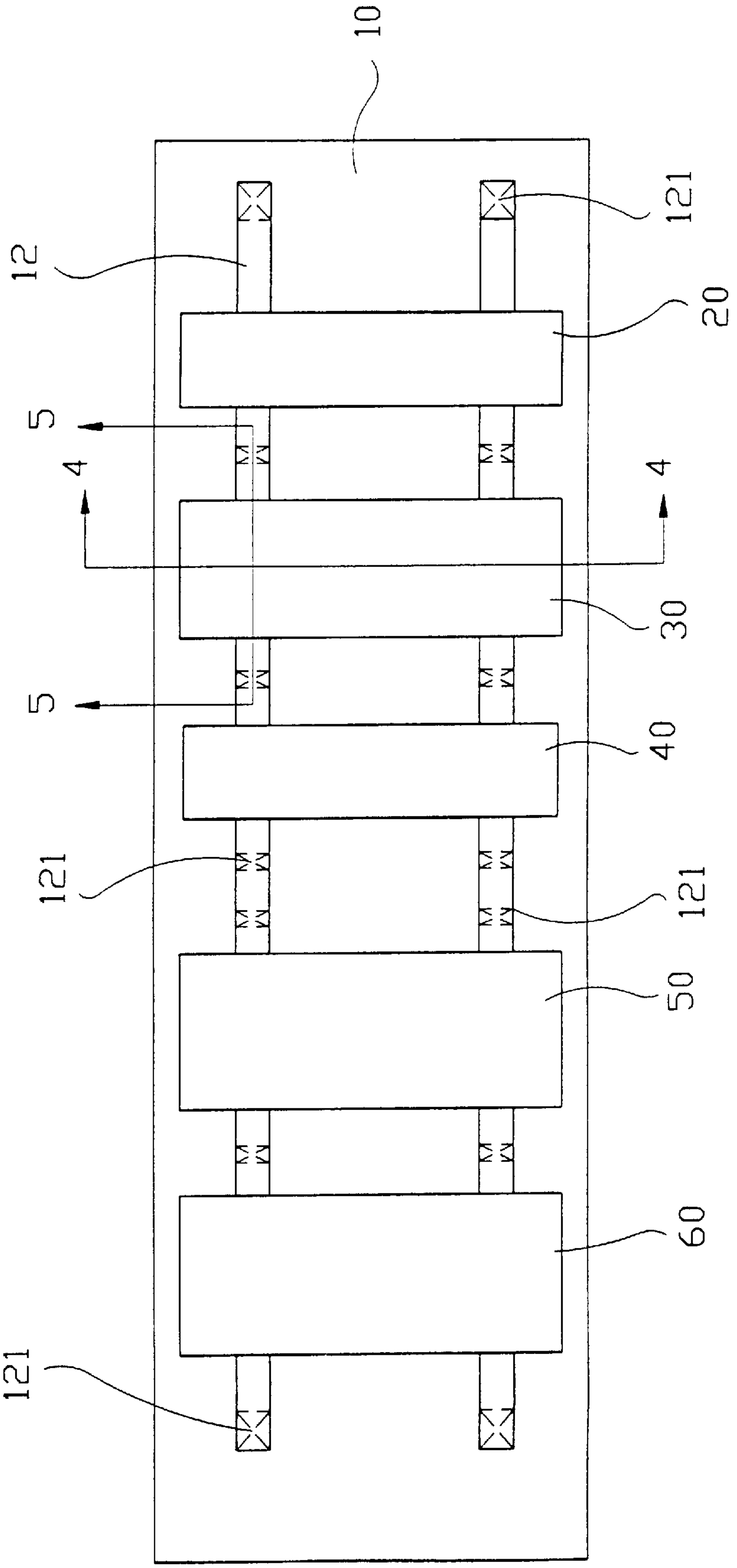
FIG. 3 is a top view of the mattress of FIG. 1.

Each of the massage units 20 thru 60 may be formed from a cloth sleeve defining a hollow space therein. Since these massage units have the same structure, only the back massage unit 30 is used as an example in the following description of the present invention. Please refer to FIGS. 2, 3 and 4. The back massage unit 30 has one or two pairs of air-cell type massage elements 70 laterally symmetrically fitted in the cloth sleeve of the back massage unit 30. An additional piece of cloth 71 is connected to the lower side of the back massage unit 30 to form the open-ended space 11 by sewing two lateral edges of the cloth 71 onto the lower side of the back massage unit 30. As mentioned above, two long locating strips 12 may be longitudinally extended through the back massage unit 30 to locate below two lateral sides of the unit 30, and the locating strips 12 are sewed onto the mattress 10 at two points separately before and after the unit 30 by a predetermined distance to form front and rear sewed lines 121, so that the unit 30 is movable between the front and the rear sewed lines 121 without separating from the mattress 10, as shown in FIG. 5. That is, the back massage unit 30 is adjustable in its longitudinal position relative to the mattress 10.

Similarly, the two long locating strips 12 extend through and locate in the lower open-ended spaces 11 below all other massage units 20, 40, 50 and 60 in the same manner, and the sewed lines 121 are provided before and after all other massage units for the latter to be position-adjustable on the mattress 10 in a longitudinal direction.

Figure 4:
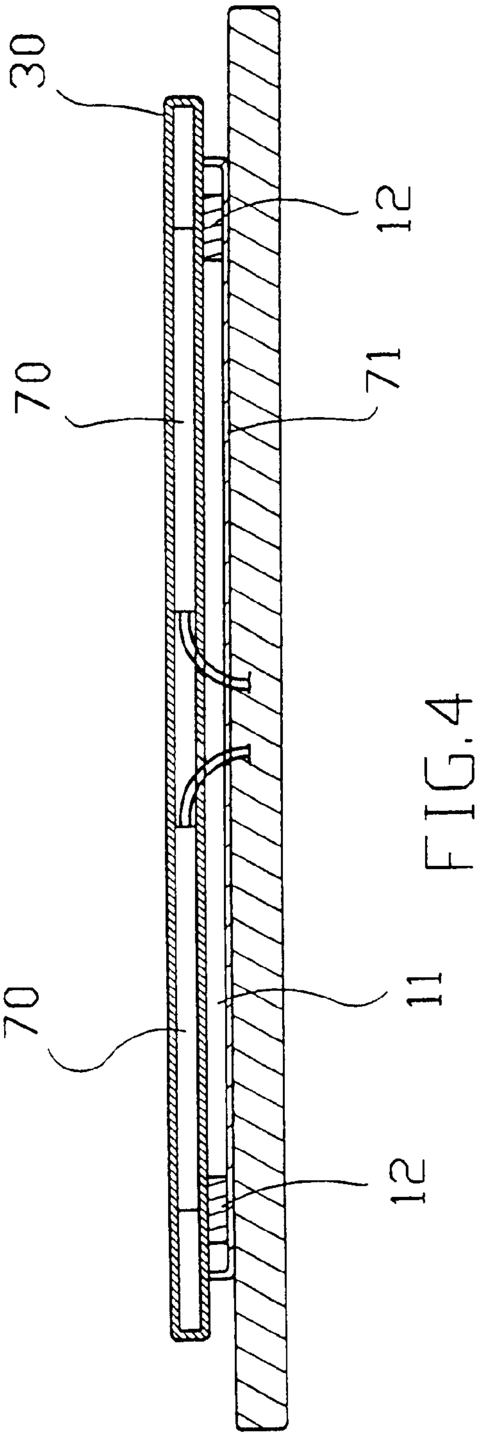
FIG. 4 is a sectional view taken on line 4—4 of FIG. 3.
Figure 5:
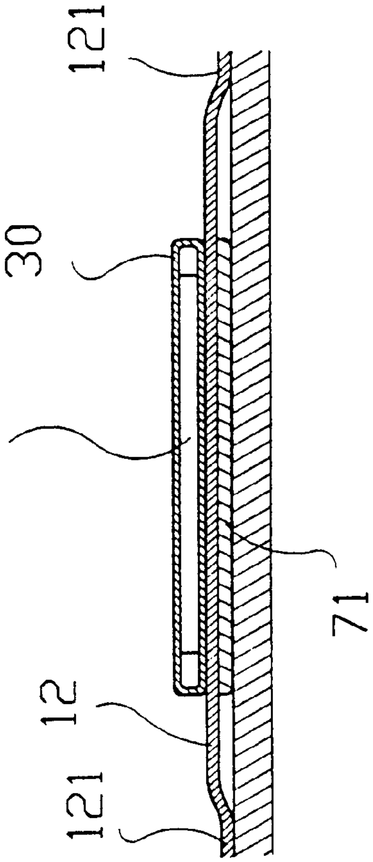
FIG. 5 is a sectional view taken on line 5—5 of FIG. 3.

Please refer to FIGS. 2 and 4. Again, the back massage unit 30 is taken as an example in the following description. Each of the air-cell type massage elements 70 has a hose 72 that extends from, for example, an inner side of the massage element 70 to downward pass through holes provided at the lower side of the back massage unit 30 and the cloth 71. The mattress 10 is provided at an area corresponding to the hoses 72 with a through hole 13, via which the hoses 72 passed through the back massage unit 30 enter into the mattress 10 before being connected to an air source (not shown). The through hole 13 may be then closed with a cover 14.

Figure 6:
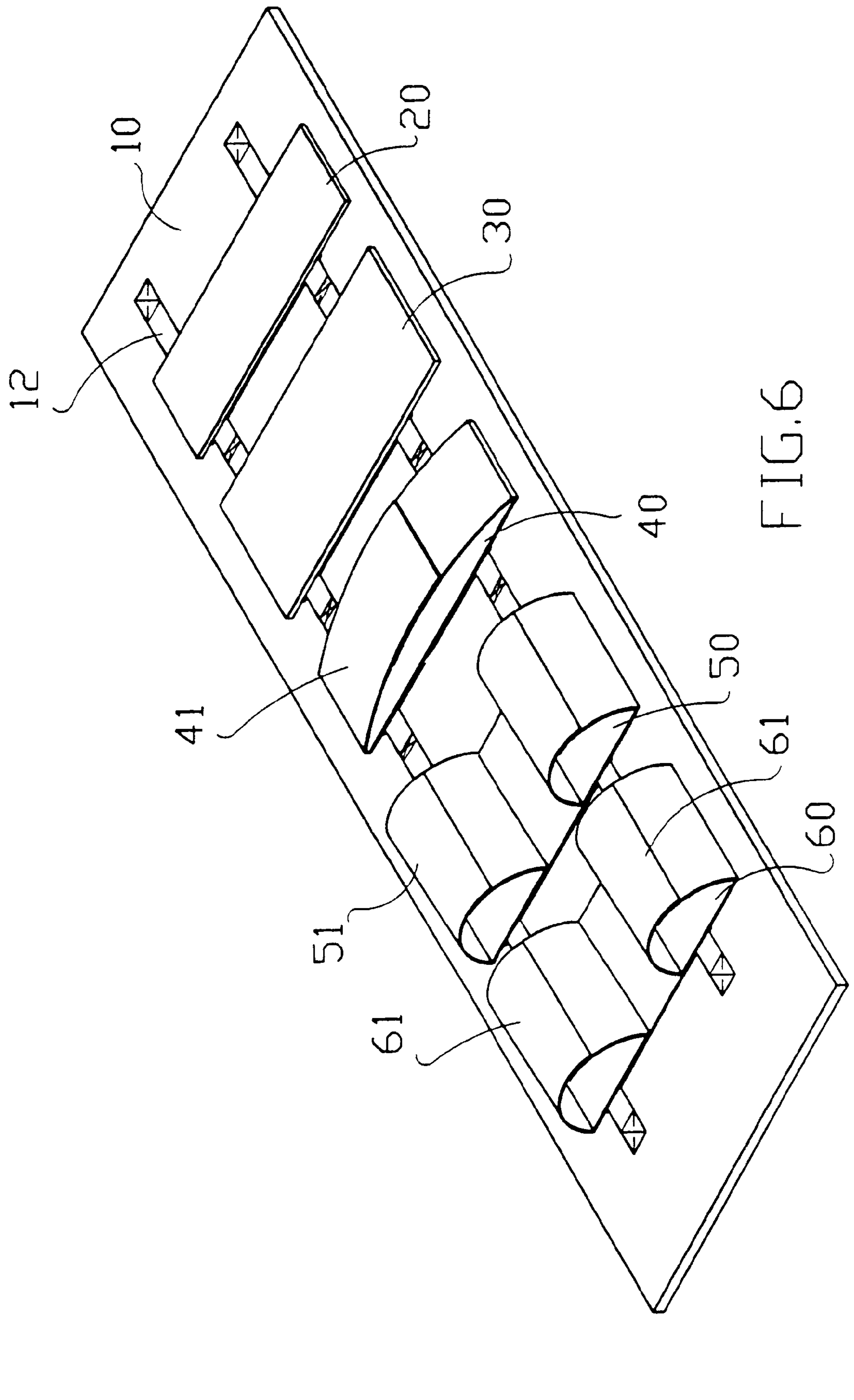
FIG. 6 is a mattress with adjustable massage units according to another embodiment of the present invention.

FIG. 6 illustrates a mattress with adjustable massage units according to another embodiment of the present invention. In this embodiment, the waist, the thigh, and the shank massage units 40, 50 and 60 are respectively provided at their upper side with binding loops 41, 51 and 61. When the air-cell type massage elements 70 (not shown in FIG. 6) arranged in the thigh and the shank massage units 50, 60 are inflated, a user's thighs and shanks (not shown) are compressed and effectively massaged separately by the binding loops 51, 61 and the cloth sleeves of the massage units 50, 60 enclosing them. The waist massage unit 40 is also provided at its upper side with a binding loop 41 suitable for binding around the user's waist. When the air-cell type massage elements 70 (not shown in FIG. 6) arranged in the waist massage unit 40 are inflated, the user's waist is subjected to a compressive force from the waist massage unit 40 and the binding loop 41. And, when the massage elements 70 are alternately inflated and deflated, the user's waist is alternately compressed and released to achieve the same effect as doing abdomen exercise. The binding loops 41, 51 and 61 all are made of soft material and changeable in their profiles. The binding loops 41, 51 and 61 shown in FIG. 6 are arch-shaped only for the purpose of illustration.

Since a distance between a man's legs and heart is large, the legs tend to suffer poor blood circulation when a man is getting old. It is known that poor blood circulation in turn causes diseases in leg blood vessels, such as varicosity, making the flow of blood returning to the heart more difficult. The binding loops 51, 61 co-operate with the thigh and the shank massage units 50, 60 to alternately compress and release the legs and would therefore be helpful in improving the blood circulation of the user's legs to reduce the probability of leg diseases.

It is understood that the massage elements 70 arranged in the massage units 20 thru 60 are not necessarily in the form of an air cell that is only a preferred embodiment of the present invention. The massage elements 70 may be otherwise in the form of a vibrator. In the case of a vibrator-type massage element 70, a wire is used to substitute for the hose 72.

The following are some of the advantages of the mattress of the present invention:

1. The numbers of massage units 20 thru 60 provided on the mattress 10 may be changed depending on the actual need of a user.
2. The massage units 20 thru 60 may be adjusted in their longitudinal position on the mattress 10 depending on the user's height.
3. The air-cell type massage elements 70 may be inflated and deflated in an operation manner preset for the mattress 10.
4. The inflated air-cell type massage elements 70 co-operate with the user's weight to press or squeeze and therefore massage muscles at two sides of the spine and on the legs.

The mattress with adjustable massage units according to the present invention can therefore meet the requirements of more people and is highly practical for use.

What is claimed is:

1. A mattress with adjustable massage units, comprising a mattress and multiple massage units attached to a top surface of said mattress; said massage units being in the form of cloth sleeves each defining a hollow space, into which at least one pair of massage elements are symmetrically arranged; said mattress being characterized in that:

each of said massage units is formed at a lower side with an open-ended space, through which two long locating strips are extended to locate near two lateral edges of said open-ended spaces, and that said two long locating strips are sewed up onto said mattress at points at a predetermined distance in front of and behind each said massage units to provide multiple sewed lines on said mattress, such that each of said massage units is longitudinally movable between two of said sewed lines before and after said particular massage unit, allowing adjustment of said massage units in their longitudinal positions relative to said mattress.

2. A mattress with adjustable massage units as claimed in claim 1, wherein said multiple massage units are so located on said mattress that they are separately suitable for massaging a user's shoulders, back, waist, thighs, and shanks.

3. A mattress with adjustable massage units as claimed in claim 1, wherein said open-ended space below each said massage unit is formed by sewing two lateral edges of an additional piece of cloth onto the lower side of said massage unit.

4. A mattress with adjustable massage units as claimed in claim 1, wherein said massage elements are air cells.

5. A mattress with adjustable massage units as claimed in claim 1, wherein said massage elements are vibrators.

6. A mattress with adjustable massage units as claimed in claim 1, wherein said massage units for massaging a user's thighs and shanks are provided at their upper sides with binding loops suitable for respectively enclosing the user's thighs and shanks therein.

7. A mattress with adjustable massage units as claimed in claim 1, wherein said massage unit for massaging a user's waist is provided at an upper side with a binding loop suitable for enclosing the user's waist therein.

* * * * *